United States Patent [19]

Berges et al.

[11] Patent Number: 5,663,177

[45] Date of Patent: Sep. 2, 1997

[54] WATER SOLUBLE CAMPTOTHECIN ANALOGS

[75] Inventors: David A. Berges, Provo, Utah; John J. Taggart, Elkins Park, Pa.

[73] Assignee: SmithKline Beecham Corporation, Philadelphia, Pa.

[21] Appl. No.: 454,793

[22] Filed: May 31, 1995

[51] Int. Cl.$^6$ ................................................ A61K 31/47
[52] U.S. Cl. ............................................ 514/279; 546/41
[58] Field of Search ................................ 514/279; 546/41

[56] References Cited

U.S. PATENT DOCUMENTS

| 4,939,255 | 7/1990 | Tagawa et al. | 546/41 |
| 5,004,758 | 4/1991 | Boehm et al. | 514/283 |
| 5,061,795 | 10/1991 | Tagawa et al. | 546/41 |

FOREIGN PATENT DOCUMENTS

| 0 296 597 | 12/1988 | European Pat. Off. . |
| 0 471 358 A1 | 2/1992 | European Pat. Off. . |
| 0 495 432 A1 | 7/1992 | European Pat. Off. . |

OTHER PUBLICATIONS

Masuda, et al., "CPT-11: A New Derivative of Camptothecin for the Treatment of Refractory or Relapsed Small-Cell Lung Cancer", (1992), *J. Clin. Oncology*, 10:1225–1229.
Wall, et al., "Plant Antitumor Agents. 30.$^{1a,b}$ Synthesis and Structure Activity of Novel Captothecin Analogs", (1993), *J. Med. Chem.*, 36:2689–2700.

*Primary Examiner*—Donald G. Daus
*Attorney, Agent, or Firm*—Yuriy P. Stercho; Stephen A. Venetianer; Edward T. Lentz

[57] ABSTRACT

The present invention provides a water soluble camptothecin analog of Formula I:

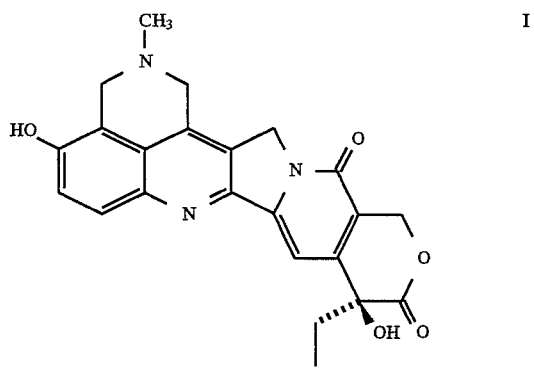

which is particularly useful as an antineoplastic agent; pharmaceutical compositions thereof; and a method of treating cancer in an animal in need thereof, including human beings, comprising inhibition of the growth of tumor cells in said animal by administration of an effective amount of a compound of Formula I.

2 Claims, No Drawings

WATER SOLUBLE CAMPTOTHECIN ANALOGS

FIELD OF THE INVENTION

The present invention relates to a water soluble camptothecin analog which is particularly useful as an antineoplastic agent, pharmaceutical compositions thereof, and methods of treatment of cancer in animals, including human beings, in need thereof comprising inhibition of the growth of tumor cells sensitive to such an analog.

BACKGROUND OF THE INVENTION

The structure of the DNA helix within eukaryotic cells imposes certain topological problems that the cellular apparatus must solve in order to use its genetic material as a template. The separation of the DNA strands is fundamental to cellular processes such as DNA replication and transcription. Since eukaryotic DNA is organized into chromatin by chromosomal proteins, the ends are constrained and the strands cannot unwind without the aid of enzymes that alter topology. It has long been recognized that the advancement of the transcription or replication complex along the DNA helix would be facilitated by a swivel point which would relieve the torsional strain generated during these processes. Topoisomerases are enzymes that are capable of altering DNA topology in eukaryotic cells. They are critical for important cellular functions and cell proliferation.

There are two classes of topoisomerases in eukaryotic cells, type I and type II. Topoisomerase I is a monomeric enzyme of approximately 100,000 molecular weight. The enzyme binds to DNA and introduces a transient single strand break, unwinds the double helix (or allows it to unwind), and subsequently reseats the break before dissociating from the DNA strand.

Topoisomerase II consists of two identical subunits of molecular weight 170,000. Topoisomerase II transiently breaks both strands of the helix and passes another double-strand segment through the break.

Camptothecin is a water-insoluble, cytotoxic alkaloid produced by *Camptotheca accuminata* trees indigenous to China and *Nothapodytesfoetida* trees indigenous to India. Camptothecin and a few close congeners thereof are the only class of compounds known to inhibit topoisomerase I.

Inhibition of topoisomerase II is the major target of important commercial oncolytic agents (e.g., etoposide, doxombicin and mitoxantrone) as well as other oncolytic agents still undergoing development. Camptothecin and its known congeners have no effect on topoisomerase II and none of the known topoisomerase II inhibitors has any significant effect on topoisomerase I.

Camptothecin and most of its analogs have not proven to be attractive for clinical drug development as cytolytic agents because of unacceptable dose limiting toxicity, unpredictable toxicity, poor aqueous solubility, unacceptable shelf life stability, and/or lack of clinical efficacy.

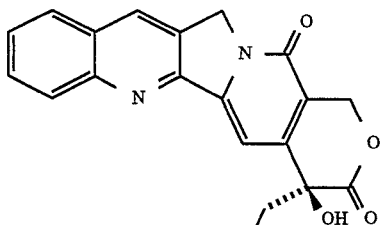

(S)-Camptothecin

However, water soluble camptothecin analogs having efficacy as topoisomerase I inhibitor antineoplastic agents are known. U.S. Pat. No. 5,004,758, issued to Boehm, et at. on Apr. 2, 1991, the specification of which is incorporated herein by reference, discloses water soluble camptothecin analogs, preferably topotecan (9-dimethylaminomethyl-10-hydroxycamptothecin), preferably (S)-topotecan, of formula:

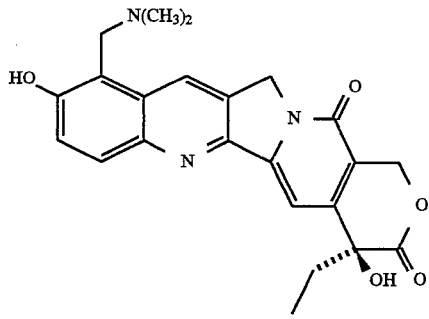

(S)-Topotecan most preferably as the hydrochloride salt. In clinical tests, topotecan has demonstrated efficacy against several solid tumor cancers, particularly ovarian cancer and non-small cell lung carcinoma in humans.

Masuda, et al., *J. Clin. Oncology,* 1992, 10, 1225–1229 describes CPT-11 (S)-[1,4'-bipiperidine]-1'-carboxylic acid, 4,11-diethyl-3,4,12,14-tetrahydro-4-hydroxy-3, 14-dioxo-1H-pyrano[3',4':6,7]indolizino[1,2-b]quinolin-9-yl However, efforts to develop CPT-11 as an antineoplastic agent have been hampered by an adverse toxicity profile.

Wall, et al., *J. Med. Chem.,* 1993, 36, 2689–2700 describes 9-aminocamptothecin ((S)-10-amino-4-ethyl-4-hydroxy-1H-pyrano[3',4':6,7]indolizino[1,2-b]quinoline-3, 14(4H,12H)-dione). However, this compound possesses limited water solubility which has posed formulation and bioavailability problems in its development as an antineoplastic agent.

There is a need for new topoisomerase I inhibiting agents which avoid the undesirable features described above. The compounds of the present invention satisfy such need.

SUMMARY OF THE INVENTION

In a first aspect, the present invention provides a compound of Formula I:

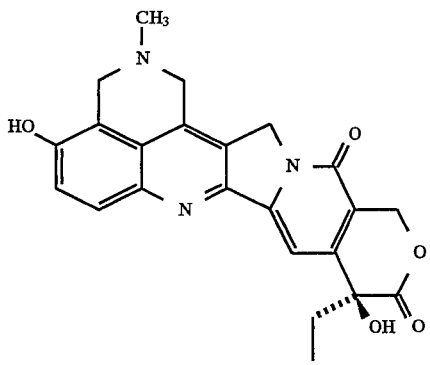

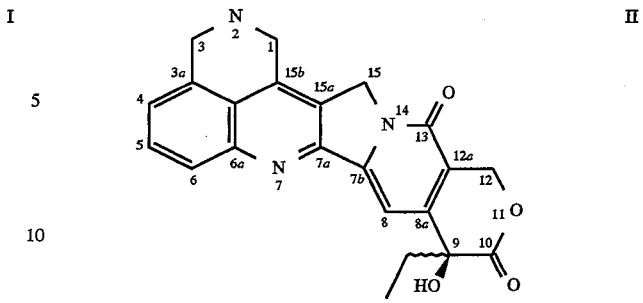

known as S-9-ethyl-2,3-dihydro-4,9-dihydroxy-2-methyl-1H,12H-benzo[ij]pyrano[3', 4':6,7]indolizino[1,2-c][2,6]naphthyridine-10,13(H,15H)-dione, and pharmaceutically acceptable salts thereof.

In another aspect, the present invention relates to pharmaceutical compositions of the compound of Formula I.

In yet another aspect, the present invention relates to methods of treatment of cancer in animals, including human beings, in need thereof comprising inhibition of the growth of tumor cells by administration of an effective amount of the compound of Formula I, alone or in combination with a carrier, diluent or excipient.

DETAILED DESCRIPTION OF THE INVENTION

The term "effective amount" means that mount of a compound or pharmaceutical composition of the present invention which, upon administration to an animal, including a human being, in need thereof for the treatment of cancer, provides a clinically desirable result in the treatment of such cancer as it is understood by one of ordinary skill in the antineoplastic treatment art, including, but not limited to, inhibition of the growth of tumor cells, remission, or cure.

Salts may be made from the compound of the present invention by reaction with its basic nitrogen. Particularly preferred are the pharmaceutically acceptable salts of the instant compound. These latter salts are those which are acceptable in their application to a pharmaceutical use. By that it is meant that the salt will retain the biological activity of the parent compound and the salt will not have untoward or deleterious effects in its application and use in treating diseases.

Pharmaceutically acceptable sails are prepared in a manner well-known to those of ordinary skill in the art. The parent compound, dissolved in a suitable solvent, is reacted with an excess of an organic or inorganic acid. Representative acids are hydrochloric acid, hydrobromic acid, sulfuric acid, phosphoric acid, acetic acid, maleic acid, succinic acid or methanesulfonic acid.

Here and throughout this application, the ring system of the compounds of the present invention is numbered according to Formula II.

If a chiral center or another form of an isomeric center is present in the compound of the present invention, all forms of such isomer or isomers are intended to be covered herein. Such compound containing a chiral center may be used as a racemic mixture, an enantiomerically enriched mixture, or the racemic mixture may be separated using well-known techniques and an individual enantiomer may be used alone.

The present invention provides a compound, and pharmaceutically acceptable salts thereof, which exhibits antineoplastic activity, said compound having the structure represented by Formula I hereinabove.

No unacceptable toxicological effects are expected when the compound of the present invention is administered in accordance with the present invention.

The present invention provides a method of treatment of cancer in an animal, preferably a mammal, most preferably a human, in need of such treatment, comprising administering to such animal an effective amount of a compound of Formula I as described hereinabove, or a pharmaceutically acceptable salt thereof, alone or in combination with a carrier, excipient or diluent.

The monohydrochloride salt of the compound of Formula I is the preferred embodiment of the present invention.

The in vitro assays used to test the compound of the present invention for antitumor activity are well-known. A generalized description of these assays follows.

CHO Microliter Cytotoxicity Assay

Chinese Hamster ovary cells are grown in Alpha MEM Medium with L-glutamine and nucleosides and containing 10% fetal bovine serum and 100 units per mL penicillin-streptomycin in 75 cm$^2$ canted neck tissue culture flasks. They are harvested from these flasks using 0.5% trypsin. Microtiter plates (96-well, sterile, flat bottom) (Corning 25860) are seeded with $1.6 \times 10^3$ wild-type (AUX-B 1) Chinese Hamster ovary cells per well or $2 \times 10^3$ multidrug resistant (CH$^R$C5) Chinese Hamster ovary cells per well. The plates are incubated at 37° C., 5% CO$_2$ overnight to allow the cells to attach. The outside wells of each plate are not used, due to evaporation during the incubation time. They are filled with medium and used as blanks. The next day, the medium is aspirated from the wells and 180 µL of fresh medium is added to each well. Compounds are diluted from stock solution in DMSO into fresh medium to a 10X concentration containing 2% DMSO. Twenty µL of this is then added to the 180 µL, of fresh medium in the wells. The plates are then incubated for another 3 days at 37° C., 5% CO$_2$. Eight mg of XTT (SIGMA X-4251) is dissolved in 100 µL of DMSO which is then added to 3.9 mL of phosphate buffered saline without cations (PBS). Phenazine methosulfate (SIGMA P-9625) is dissolved in PBS to a concentration of 3 mg/mL and 20 µL of this is added to the XTT solution. Fifty µL of this XTT/PMS solution is added to each well of the microliter plate and the plates are incubated for 90 minutes at 37° C., 5% $CO_2$ (until the $OD_{450}$~1.0). The plate is then read on a UV Max plate reader, using wells without cells (i.e., containing only 200 μL of medium and 50 μL of XTT/PMS solution) as a background control.

The cytotoxicity and efficacy of the compound of the present invention was also tested in vivo using the well-known P388 mouse tumor model.

Table I provides a comparison of the cytotoxicity and efficacy in mouse tumor models of the compound of Formula I with the known compounds topotecan and camptothecin. These results demonstrate that the compound of Formula I possesses biological activity comparable to topotecan.

TABLE I

| SB No. | Cytotoxicity $IC_{50}$ (μM) | | | Efficacy in Mouse Tumor Models % Inc. in |
|---|---|---|---|---|
| | Wildtype (AUX-B1) | Multidrug Resistant | P388 | Lifespan/Dose (mg/kg) P388 |
| Topotecan | 0.79 | 2.3 | 0.03 | 156/14.4 |
| Camptothecin | 0.015 | 0.035 | 0.012 | |
| Formula I | 0.052 | 0.84 | 0.024 | 111/40 ip |

The compound of Formula I is prepared by the method described in Scheme I. The hydroxy group of 10-hydroxycamptothecin 1, which is readily available from camptothecin by the process described in U.S. Pat. No. 5,004,758, is protected as an ester, for example as a propionate ester 2, by reaction with an acylating agent such as propionic anhydride in the presence of a base such as pyridine. Treatment of 2 in N,N-dimethylformamide with a free-radical generating reagent such as benzoyl peroxide in the presence of an acid such as trifluoroacetic acid followed by chromatography on silica gel with methanol in the solvent produces formamide 3 which is deformylated by heating with a strong acid such as hydrochloric acid in methanol. The resulting amine 4) is then treated with formaldehyde in aqueous acetic acid to effect a Pictet-Spengler cyclization giving the compound of Formula I.

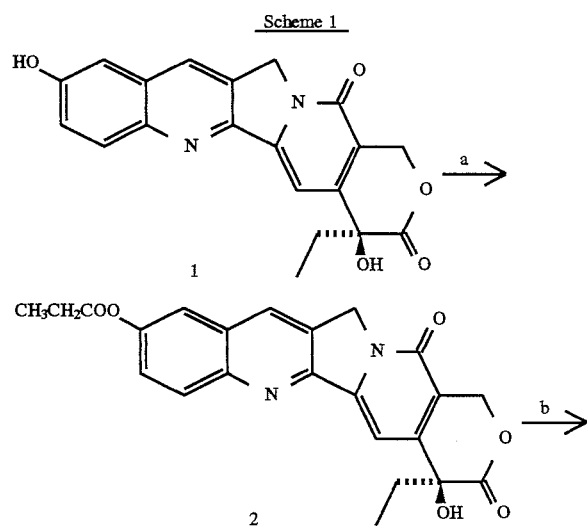

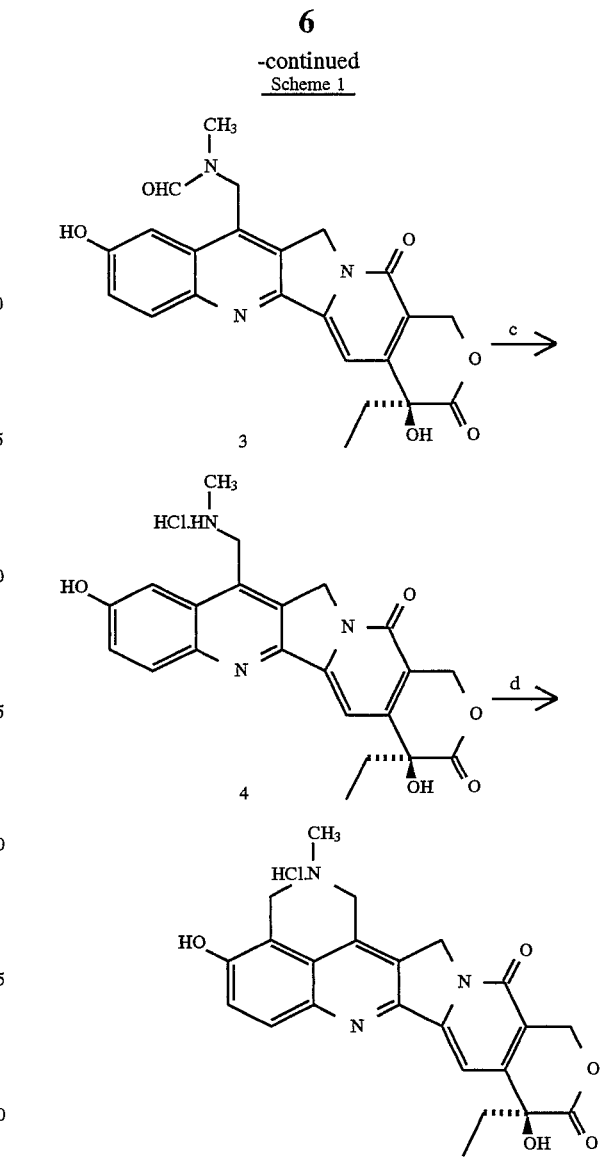

a) $(CH_3CH_2CO)_2O$, pyridine, DMF;
b) $(C_6H_5CO)_2O_2$, TFA, DMF, 85° C. and then $CH_3OH$, silica gel;
c) 12 N HCl in $CH_3OH$(1:19), reflux;
d) HCHO, $CH_3COOH$, $H_2O$, 70° C.

The present invention provides pharmaceutical compositions prepared from the compound of Formula I. These compositions have both a human and a veterinary utility, and comprise an excipient, diluent, or carrier which is acceptable for the intended pharmaceutical end use and the inventive compound. For example, if a veterinary use is intended, the carrier may be a liquid, or spray, or may be formulated in a solid, non-degradeable or degradeable form for insertion in the rumen. Selected excipients and carriers may be employed to prepare compositions acceptable or adaptable for human use.

An effective amount of one or more pharmaceutical compositions of the present invention may be contained in one embodiment, such as in a single pill, capsule, or pre-measured intravenous dose or pre-filled syringe for injection. Alternatively, as is frequently the case, the composition will be prepared in individual dose forms where one unit, such as a pill, will contain a sub-optimal dose but the user will be instructed to take two or more unit doses per treatment. When the composition is presented as a cream, it will contain a discrete amount of drug and the user will apply some amount of the cream one or more times until the disease is in remission or has been effectively treated. Concentrates for later dilution by the end user may also be prepared, for instance for intravenous (IV) formulations and multi-dose injectable formulations.

Excipients, diluents, or carriers contemplated for use in these compositions are generally known in the pharmaceutical formulary arts. Reference to useful materials can be found in well-known compilations such as *Remington's Pharmaceutical Sciences*, Mack Publishing Co., Easton, Pa.

The nature of the composition and the pharmaceutical excipient, diluent or carrier will, of course, depend upon the intended route of administration, for example whether by intravenous and intramuseular injection, parenterally, topically, orally, or by inhalation.

For parenteral administration the pharmaceutical composition will be in the form of a sterile injectable liquid such as an ampule or an aqueous or nonaqueous liquid suspension.

For topical administration the pharmaceutical composition will be in the form of a cream, ointment, liniment, lotion, paste, spray or drops suitable for administration to the skin, eye, ear, nose or genitalia.

For oral administration the pharmaceutical composition will be in the form of a tablet, capsule, powder, pellet, troche, lozenge, syrup, liquid, or emulsion.

The pharmaceutical excipient, diluent or carrier employed may be either a solid or liquid. When the pharmaceutical composition is employed in the form of a solution or suspension, examples of appropriate pharmaceutical carriers or diluents include: for aqueous systems, water; for non-aqueous systems: ethanol, glycerin, propylene glycol, olive oil, corn oil, cottonseed oil, peanut oil, sesame oil, liquid paraffins, and mixtures thereof with water; for solid systems: lactose, terra alba, sucrose, talc, gelatin, agar, pectin, acacia, magnesium stearate, stearic acid, kaolin and mannitol; and for aerosol systems: dichlorodifluoromethane, chlorotrifluoroethane and compressed carbon dioxide. Also, in addition to the pharmaceutical carrier or diluent, the instant compositions may include other ingredients such as stabilizers, antioxidants, preservatives, lubricants, suspending agents, viscosity modifiers and the like, provided that the additional ingredients do not have a detrimental effect on the therapeutic action of the instant compositions. Similarly, the carrier or diluent may include time delay material well known to the art, such as glyceryl monostearate or glyceryl distearate alone or with a wax, ethylcellulose, hydroxypropylmethylcellulose, methylmethacrylate and the like.

A wide variety of pharmaceutical forms can be employed. Thus, if a solid carrier is used, the preparation can be tableted, placed in a hard gelatin capsule in powder or pellet form or in the form of a troche or lozenge. The amount of solid carrier will vary widely but preferably will be from about 25 mg to about 1 gram. If a liquid carrier is used, the preparation will be in the form of a syrup, emulsion, soft gelatin capsule, sterile injectable solution Or suspension in an ampule or vial or nonaqueous liquid suspension. To obtain a stable water soluble dose form, a pharmaceutically acceptable salt of the compound of Formula I is dissolved in an aqueous solution of an organic or inorganic acid or base. If a soluble salt form is not available, the compound of Formula I may be dissolved in a suitable co-solvent or combinations thereof. Examples of such suitable cosolvents include, but are not limited to, alcohol, propylene glycol, polyethylene glycol 300, polysorbate 80, glycerin and the like in concentrations ranging from 0–60% of the total volume.

It will be appreciated that the actual preferred dosages of the compound used in the compositions and methods of treatment of the present invention will vary according to the particular complex being used, the particular composition formulated, the mode of administration and the particular site, host and tumor type being treated. Optimal dosages for a specific pathological condition in a particular patient may be ascertained by those of ordinary skill in the antineoplastic art using conventional dosage determination tests in view of the above experimental data. For parenteral administration, the dose of the compound of Formula I generally employed is from about 2 to about 50 mg/m$^2$ of body surface area per day for one to five days, preferably repeated about every fourth week for four courses of treatment. For continuous intravenous administration, the dose generally employed is about 0.5 mg/m$^2$/day for 5 to 21 days. For oral administration, the dose generally employed is about 20 to about 150 mg/m$^2$ of body surface area per day for one to five days, with courses of treatment repeated at appropriate intervals.

EXAMPLES

In the following synthetic examples, temperature is in degrees Centigrade (°C.). Unless otherwise indicated, all of the starting materials were obtained from commercial sources. Without further elaboration, it is believed that one skilled in the art can, using the preceding description, utilize the present invention to its fullest extent. These Examples are given to illustrate the invention, not to limit its scope. Reference is made to the claims for what is reserved to the inventors hereunder.

EXAMPLE 1

Preparation of (S)-9-Ethyl-2,3-dihyro-4,9-dihydroxy-2-methyl-1H,12H-benzo [ij]pyrano[3',4':6,7]indolizino[1,2-c] [2,6]naphthyridine-10,13(9H,15H)-dione monohydrochloride monohydroacetate monohydrate a) (S)-10-Propanoyloxycamptothecin (S)-10-Hyctroxycamptothecin (3.93 g, 0.0108 mol) in dry DMF (100 mL) and dry pyridine ( 8.5 mL) was treated in one portion with propanoic anhydride (1.48 g, 0.0114 mol). The solution was stirred for several hours. More propanoic anhydride (0.370 g, 0.00285 mol) was added, and the solution was stirred for an additional 5 h. The reaction mixture was evaporated to dryness under reduced pressure, and the residue was partitioned between methylene chloride and water. The layers were separated, and the aqueous phase was re-extracted with methylene chloride. The combined organic layer was dried (sodium sulfate) and filtered, and the filtrate was concentrated to afford a yellow-ecru solid. This solid was triturated with methanol to afford the title compound as a tan-ecru solid (3.89 g, 86%). 1H NMR (400 MHz, CDCl$_3$), δ 8.40 (s, 1H), 8.20 (d, J=9.2, 1H), 7.71 (d, J=3.3, 1H), 7.56 (dd, J=9.2, J=2.3, 1H), 5.68 (d, J=16.3, 1H), 5.31 (d, J=16.3 Hz, 1H), 5.30 (s, 2H), 3.86 (s, 2H), 2.71 (q, J=7.5 Hz, 2H), 1.93 (m, 2H), 1.33 (t,J=7.4 Hz, 3H).

b) (S)-7-N-Formyl-N-methylaminomthyl-10-hydroxycamptothecin

A stirred suspension of (S)-10-propanoyloxycamptothecin (2.00 g, 0.00476 mol) and dry DMF (100 mL) was treated with trifluoroacetic acid (0.92 mL, 0.012 mol). The resulting clear solution was then treated with benzoyl peroxide (1.15 g, 0.00476 mol). The solution was warmed to 85° C., stirred for 6 h, and evaporated to a dark amber residue which was chromatographed on silica gel (gradient from methylene chloride to 96.5:3.5 methylene chloride:methanol). Fractions containing the desired product were pooled, evaporated to dryness, and sonicated with methanol (6 mL) The resulting solid was collected and dried in vacuo to afford the title compound as a tan solid (64 mg, 3.1%). $^1$H NMR (400 MHz, CDCl$_3$+ CD$_3$OD) δ 8.18 (s, 1H), 8.08 (d, J=9.2, 1H), 7.65 (s, 1H), 7.37–7.46 (m, 2H), 5.67 (d, J=16, 1H), 5.31 (s, 2H), 5.30 (d, J=16, 1H), 5.07 (s, 2H), 2.87 (s, 3H), 1.93 (m, 2H), 1.03 (t, J=7.3 Hz, 3H).

c) (S)-7-Methylaminomethyl-10-hydroxycamptothecin hydrochloride (S)-7-N-Formyl-N-methylaminomethyl-10-hydroxycamptothecin (32 mg, 0.0735 mmol) was suspended in 5% HCl in methanol (5 mL). The mixture was heated at just below reflux temperature for 1 h and then cooled in ice, and a solid was collected, washed sparingly with cold methanol, and dried in vacuo to afford 20.2 mg of the title compound. A second crop (5 mg, 84% total yield) was obtained by allowing the filtrate to stand overnight at room temperature. $^1$H NMR (400 MHz, CDCl$_3$+CD$_3$OD) δ 8.16 (d, J=9.1 Hz, 1H), 7.68 (s, 1H), 7.55 (dd, J =9.1 Hz and J=2.0 Hz, 1H), 7.49 (t, J=2.0 Hz, 1H), 5.63 (d, J=16.3 Hz, 1H), 5.48 (s, 2H), 5.35 (d, J=16.3 Hz, 1H), 4.71–4.80 (m, 2H), 2.85 (s, 3H), 1.97 (m, 2H), 1.03 (t, J=7.4 Hz, 3H).

d) (S)-9-Ethyl-2,3-dihyro-4,9-dihydroxy-2-methyl-1H, 12H-benzo [ij]pyranol[3',4':6,7]indolizino[1,2-c][2,6] naphthridine-10,13(9H,15H)-dione monohydrochloride monohyrdoacetate monohydrate (S)-7-Methylaminomethyl-10-hydroxycamptothecinohydrochloride (20 mg, 0.0416 mmol) in acetic acid (4 mL) and water (1 mL) was treated with 37% formaldehyde solution (72 μL). The solution was stirred at 75° C. for 5 h and evaporated to dryness. The residue was taken up in water and subjected to MPLC (Partisil 40 ODS-3 using a gradient from:water with 0.1% acetic acid to 7:3 water-methanol with 0.1% acetic acid). The effluent was monitored at 254 nm, and product-containing fractions were pooled, concentrated in vacuo to 3 mL and treated with 10 μL of 0.1 N HCl solution. This solution was lyophilized to give a canary colored solid (15.8 mg, 68%) $^1$H NMR (400 MHz, CDCl$_3$+CD$_3$OD) δ 7.85–7.95 (m,1H), 7.63 (s,1H), 7.30–7.45 (m, 1H), 5.65 (d, J=16 Hz, 1H), 5.30 (d, J=16 Hz, 1H), 5.18 (s, 2H), 3.97 (s,2H), 3.35 (s, 2H), 2.72 (s, 3H), 2.05 (s, 3H), 1.85–1.98 (m, 2H), 1.03 (t, J=7.3 Hz, 3H); MS (electrospray ionization) m/e 420 [M+H]+; Anal.: (C$_{23}$H$_{21}$N$_3$O$_5$oHCloC$_2$H$_4$O$_2$oH$_2$O) calcd.: C, 56.23; H, 5.29; N, 7.87. found: C, 55.97; H, 4.97; N, 7.72.

EXAMPLE 2

Parenteral Composition

To prepare a parenteral pharmaceutical composition of this invention suitable for administration by injection, 100 mg of a water soluble salt of a compound of Formula I is mixed with 10 ml of 0.9% sterile saline, and the mixture is incorporated into a dosage unit form suitable for administration by injection.

EXAMPLE 3

Oral Composition

To prepare an oral pharmaceutical composition of this invention, 100 mg of a compound of Formula I is mixed with 750 mg of lactose, and the mixture is incorporated into an oral dosage unit form, such as a hard gelatin capsule, which is suitable for oral administration.

Although the above specification and Examples fully describe the present invention, particularly the preferred embodiments thereof, it is understood that the present invention is not limited to these particular disclosed embodiments. Thus, the present invention includes all embodiments coming within the scope of the following claims.

We claim:

1. A compound of Formula I:

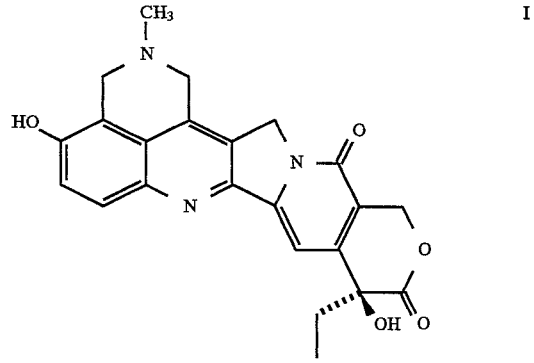

known as S-9-ethyl-2,3-dihydro-4,9-dihydroxy-2-methyl-1H,12H-benzo [ij]pyrano[3',4':6,7]indolizino[1,2-c][2,6] naphthyridine-10,13(H,15H)-dione, and pharmaceutically acceptable salts thereof.

2. A pharmaceutical composition comprising a compound of Formula I:

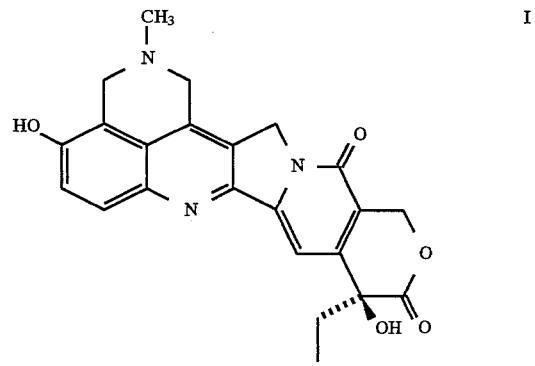

known as S-9-ethyl-2,3-dihydro-4,9-dihydroxy2-methyl-1H,12H-benzo [ij]pyrano[3',4':6,7]indolizino[1,2-c][2,6] naphthyridine-10,13(H,15H)-dione, or a pharmaceutically acceptable salt thereof, in combination with a pharmaceutically acceptable carrier, diluent or excipient.

* * * * *